United States Patent [19]

Hirama

[11] Patent Number: 4,716,765
[45] Date of Patent: Jan. 5, 1988

[54] ULTRASONIC MEASURING APPARATUS

[75] Inventor: Makoto Hirama, Ootawara, Japan

[73] Assignee: Kabushiki Kaisha Toshiba, Kawasaki, Japan

[21] Appl. No.: 891,891

[22] Filed: Aug. 1, 1986

[30] Foreign Application Priority Data

Aug. 9, 1985 [JP] Japan .................. 60-176113

[51] Int. Cl.$^4$ ............................................. G01N 29/00
[52] U.S. Cl. ........................................ 73/626; 73/597;
73/625; 128/660
[58] Field of Search .................... 73/626, 625, 597;
367/58, 59; 128/660

[56] References Cited

U.S. PATENT DOCUMENTS

| | | | |
|---|---|---|---|
| 3,381,266 | 4/1968 | Harris | 367/59 |
| 4,070,905 | 1/1978 | Kosoff | 73/629 |
| 4,330,872 | 5/1982 | Bratton | 367/59 |
| 4,417,475 | 11/1983 | Okazaki | 73/626 |
| 4,566,459 | 1/1986 | Umemura et al. | 73/626 |

OTHER PUBLICATIONS

*Encyclopedic Dictionary of Exploration Geophysics,* Sheriff, 1974, p. 155.

Primary Examiner—Howard A. Birmiel
Attorney, Agent, or Firm—Finnegan, Henderson Farabow, Garrett & Dunner

[57] ABSTRACT

An ultrasonic measuring apparatus having an ultrasonic transducer array for transmitting ultrasonic beams and receiving echoes corresponding to the beams. The array is divided into a transmission section and a reception section. The transducer elements of the transmission section emit sequentially ultrasonic beams at a predetermined angle to a plurality of targets in a subject. The elements of the reception section receives echoes corresponding to the ultrasonic beams and coming at a predetermined angle, i.e., from the direction crossing the transmission ultrasonic beam and converts the echoes to echo signals. The echo signals are added or averaged, thereby obtaining the time which ultrasonic waves require to propagate through the subject. The sound velocity at which the ultrasonic waves travel in the subject is calculated from this propagation time.

8 Claims, 5 Drawing Figures

ULTRASONIC MEASURING APPARATUS

BACKGROUND OF THE INVENTION

The present invention relates to an ultrasonic measuring apparatus, and more particularly to an ultrasonic measuring apparatus for applying crossing ultrasonic beams to a subject, thereby measuring the sound velocity of the ultrasonic waves propagating through the subject.

Various methods have been proposed wherein ultrasonic waves are applied to the region of interest of a living subject to obtain data showing the conditions of tissues in the region of interest. Of these methods, the so-called cross beam method is drawing particular attention. In this method, an ultrasonic transmission beam and an ultrasonic echo beam are applied, crossing each other, to a subject to obtain various acoustic parameters and various nonlinear parameters showing the condition of the region of interest.

Ultrasonic diagnosis apparatuses employing the cross beam method are disclosed in U.S. patent application Ser. No. 835,195 and also in the U.S. patent application filed on June 18, 1986, claiming priority based on Japanese Patent Application No. 60-133421. Both apparatuses use a linear steering type ultrasonic transducer. The ultrasonic transducer of this type comprises an array of a number of ultrasonic transducer elements. The elements are divided into a first group and a second group. These transducer groups are set apart for a predetermined distance. When the first transducer group is used as a beam transmission unit, drive pulses generated at different times are supplied to the ultrasonic transducer elements of the first group. Driven by these pulses, the transducer elements emit an ultrasonic beam at a specific angle to a region of interest. The second transducer group receives the ultrasonic waves reflected from the region of interest, called "echoes." The period between the emission of the ultrasonic beam and the receipt of the echo wave, which corresponds to the beam, is measured. From this period, or the propagation time, the sound velocity of the ultrasonic wave propagating in the subject is calculated. This sound velocity is used in diagnosing the subject.

In the conventional ultrasonic diagnosis apparatus described above, the signal obtained by each beam transmission and each wave reception contains unwanted components called "ripples." The ripples are generated when the ultrasonic beam scatters, causing a phenomenon known as "speckle," at points in the region of interest, other than the point which the axis of the beam passes. Due to the ripples, the propagation velocity of the ultrasonic wave cannot be accurately measured. In order to eliminate the ripples, the transducer array can be moved while transmitting beams and receiving echoes, thus obtaining more data, and the data can then be averaged. For the same purpose, a large quantity of data can be obtained from the echoes reflected from the tissues moving due to the heart beats or the motion of the lungs, and is then averaged.

The first method of eliminating the ripples is disadvantageous in two respects. First, the distance between the subject and the ultrasonic transducer array inevitably changes, whereby the data obtained is not sufficiently accurate. Secondly, the operator tends to move the array away from a B-Mode image observation region.

The second method of eliminating speckles is also disadvantageous. Although the second method does not have the problems inherent in the first method, it cannot provide sufficient data within a short time since the tissues cannot move as quickly as desired.

SUMMARY OF THE INVENTION

The object of the present invention is to provide an ultrasonic measuring apparatus which can accurately measure the sound velocity of ultrasonic waves propagating through a subject, without being affected by speckle, and which can therefore efficiently serve in diagnosing the subject.

The present invention uses an array of ultrasonic transducer elements. The elements are divided into two groups. Drive pulses are supplied at different times to the transducer elements of the first group. The transducer elements of the first group emit ultrasonic beams to a target in the region of interest of a subject, and the transducer elements of the second group receive echoes from the target and converts them into an echo signal. Then, the elements of the first group emit other ultrasonic beams to the next target in the region of interest, and the elements of the second group receive echoes emitted from this target and converts it to an echo signal. Further, the array sequentially emits ultrasonic beams to other points existing at regular intervals in a certain direction in the region of interest and receives echoes from these targets, and sequentially generates echo signals corresponding to these echoes. Echo signals are added, or averaged. The sound velocity at which ultrasonic waves have propagated in the subject is calculated from the sum of the signals or the average value thereof.

DETAILED DESCRIPTION OF THE PREFERRED EMBODIMENTS

Figure 1:
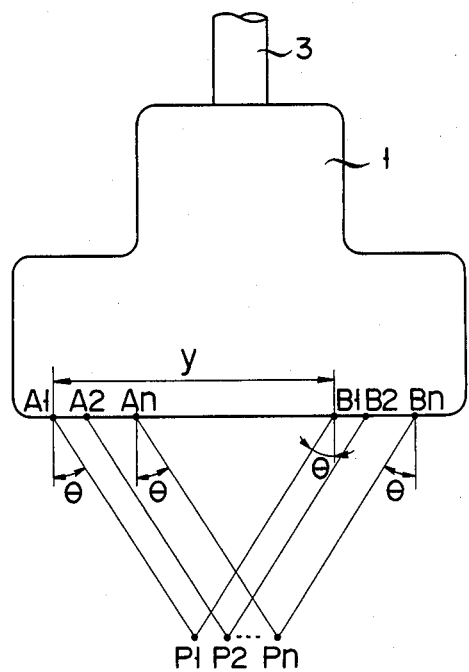
FIG. 1 is a diagram explaining how the ultrasonic transducer of an ultrasonic imaging arrangement including an ultrasonic measuring apparatus according to the invention performs cross beam steering.

FIG. 1 is a schematic diagram explaining how the ultrasonic transducer 1 of an ultrasonic imaging apparatus of the invention applies cross beams to a subject to obtain data about the region of interest of the subject. Transducer 1 comprises an array of 128 ultrasonic transducer elements.

The first 32 transducer elements T1–T32 (FIG. 3), are first driven, whereby transducer 1 emits a first transmission ultrasonic beam to target P1 existing in the region of interest. The axis of the first beam passes through the midpoint of the array of elements T1–T32 and is inclined at angle $\theta$ to the perpendicular passing midpoint A1. The echo, i.e., the ultrasonic beam reflected from target P1, propagates to other 32 elements T65–T96. The axis of this ultrasonic beam passes midpoint B1 of the array of elements T65–T96 and is inclined in a direction crossing the first ultrasonic beam, i.e., at angle $\theta$ to the perpendicular passing midpoint B1. Then, transducer elements T2–T33 are driven, whereby transducer 1 emits a second ultrasonic beam to target P2 next to target point P1. The axis of second beam passes midpoint A2 of the array of elements T2-T33 and is inclined at angle $\theta$ to the perpendicular passing midpoint A2. The echo from target P2, propagates to other elements T66-T97. The axis of this ultrasonic beam passes midpoint B2 of the array of elements T66-T97 and is inclined in a direction crossing the second ultrasonic beam, i.e., at angle $\theta$ to the perpendicular passing midpoint B2. Thereafter, ultrasonic transducer 1 emits ultrasonic beams to other targets P3, P4 . . . Pn, as its selected ultrasonic elements are sequentially repeated, 32 elements at a time as described above, and echoes propagate from points P3, P4 . . . Pn to transducer 1. As transducer 1 receives echoes from targets P1 to Pn, it sequentially generates echo signals.

Figure 2A:
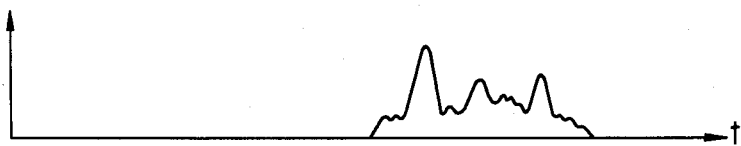
FIGS. 2A to 2C show the drive voltage applied to the ultrasonic transducer and the waveforms of the echo signals the transducer receives.
Figure 2B:
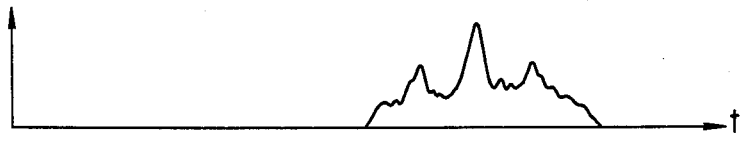

The ultrasonic beam at the cross point of the transmission ultrasonic beam and echo has a width of a given value. The transmission ultrasonic beam inevitably scatters, causing a speckle, at the points other than the target, which exist in the region of interest. The echo signal obtained from the echo inevitably contains undesirable components, ripples, resulting from the speckle. Due to the ripples, the echo signals obtained from different targets have different waveforms, as is shown in FIGS. 2A and 2B. The echo signals generated by transducer 1 and corresponding to different targets are added, or averaged, whereby an echo signal having the waveform shown in FIG. 2C, containing no ripples, can be obtained.

To remove ripples efficiently from the echo signal, the ultrasonic beams must be emitted into the subject at such an angle that the ultrasonic waves being reflected at the centers of scattering (i.e., the centers of targets) of the beams require substantially the same time to travel from the transmission section of the transducer to the targets and then to the reception section of the transducer. To fulfill this requirement, ultrasonic transducer 1 is driven such that distance y (FIG. 1) between every beam-emitting point (A) and the corresponding beam-receiving point (B) is equal, and that the angle between the transmission ultrasonic beam and echo has a constant value.

Figure 2C:
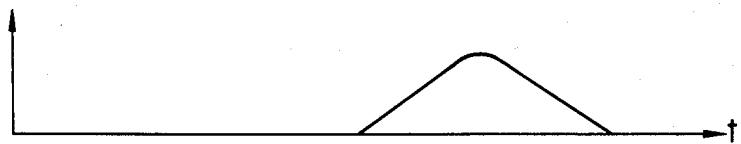

Sound velocity C, at which the ultrasonic waves propagate from the beam-emitting transducer elements to the targets and from the targets to the beam-receiving transducer elements, is given by the following equation and calculated from the echo signal having the waveform of FIG. 2C:

$$C = y/(t \cdot \sin \theta) \quad (1)$$

where t is the time the ultrasonic wave requires to propagate from target A to target B.

Figure 3:
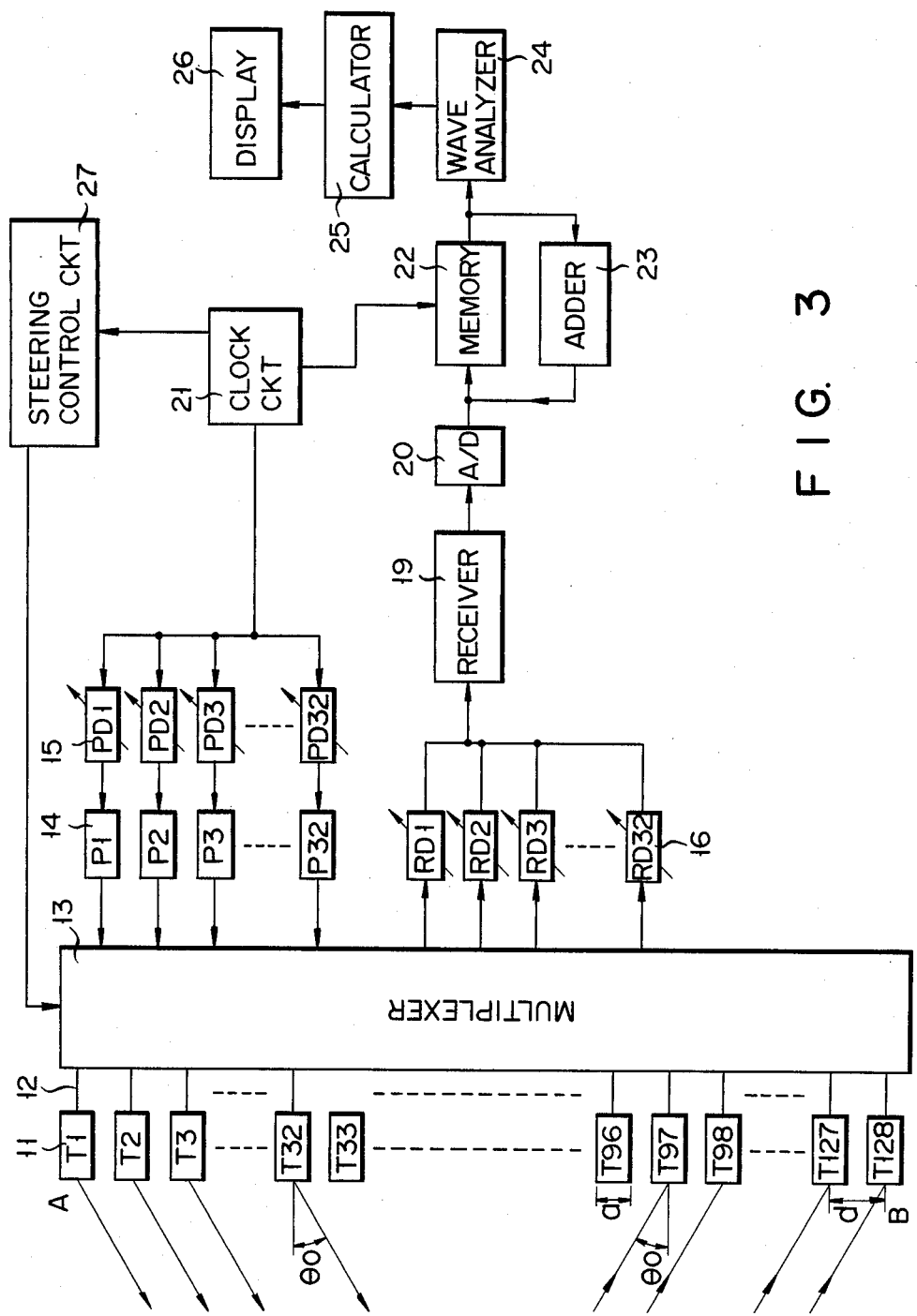
FIG. 3 is a block diagram showing the ultrasonic imaging apparatus.

FIG. 3 is a block diagram showing an ultrasonic measuring apparatus according to the invention. As this figure shows, 128 transducer elements T1-T128 are provided on the wave emission/reception surface 2 of transducer 1 and form an array 11. Elements T1-T128 each have a width of 0.45 mm and are arranged in a line at regular intervals d of 0.5 mm, and are coupled to multiplexer 13 by lead wires 12 of one cable 3 (FIG. 1).

A clock circuit 21 is provided which has a pulse generator and a frequency divider. The pulse generator generates a reference clock signal having a frequency of 10 MHz. The frequency divider divides the frequency of the clock signal, thus generating rate pulses at the frequency of 4 KHz. The output terminal of circuit 21 is connected to transmission delay elements PD1-PD32, which in turn are connected to 32 pulsers P1-P32. The output terminals of the pulsers are coupled to multiplexer 13. When transducer 1 is put in contact with the material coated on the subject, and multiplexer 13 connects pulsers P1-P32 to ultrasonic transducer elements T1-T32, elements T1-T32 emits an ultrasonic wave into the subject. Let us assume that the ultrasonic wave travels in the subject at sound velocity $C_0$ of 1530 m/s. To emit an ultrasonic beam at angle $\theta_0$, each transducer element must be driven such that one element after the preceding element with a time delay $\theta_0$ given as:

$$\tau_0 = (d/C_0) \cdot \sin \theta_0 \quad (2)$$

Delay time $\tau_0$ is determined by transmission delay elements PD1-PD32 of transmission delay circuit 15. More precisely, delay time of 0 is set in element PD1, delay time of $\tau_0$ is set in element PD2, delay time of 2 $\tau_0$ is set in element PD3, and so forth. Hence, delay time of 31 $\tau_0$ is set in the last transmission delay element PD32. Actually, the ultrasonic wave emitted from each transducer element propagate in the subject at sound velocity C different from sound velocity $C_0$. Hence, the ultrasonic beam is emitted at angle $\theta$, not angle $\theta_0$. From the Snell law of refraction, angle $\theta$ is given as:

$$\sin \theta / C = \sin \theta_0 / C_0 \quad (3)$$

Multiplexer 13 connects transducer elements T65-T96 to reception delay elements DR1-RD32 of reception delay circuit 16. Delay time of 31 $\tau_0$ is set in element DR1, and delay time of 30 $\tau_0$ is set in element DR2, and so forth. Delay time of 0 is set in the last reception delay element DR32.

The ultrasonic beam emitted from ultrasonic transducer elements T1-T32 is reflected from region P of interest. Array 11 receives the echo from region P. If the ultrasonic wave is propagated in the subject at sound velocity $C_0$, the echo is incident on array 11 at angle $\theta_0$. In fact, the echo wave propagates in the subject at sound velocity C. Hence, the wave is incident on array 11 at angel $\theta_0$. Ultrasonic transducer elements T65-T96 receive the echo and convert it to an echo signal having directivity (angle $\theta_0$). The echo signal is input to receiver circuit 19.

The echo signal is detected and amplified by receiver circuit 19 and is then converted to a digital signals by A/D converter 20. The digital signals are stored in frame memory 22. Memory 22 is address-controlled by the 10-KHz clock signal obtained by processing the rate pulses generated by clock circuit 21. Hence, the addresses where the sampled components of the echo wave are stored are identical with the addresses where the components sampled from the echo wave at intervals of 100 nano seconds (ns) from the time array 12 emits the ultrasonic beam.

Multiplexer 13 is controlled by steering control circuit 27 to select and drive 32 transducer elements for emitting an ultrasonic beam and also to select other 32 transducers for receiving the echo corresponding to the beam. More specifically, multiplexer 13 first drives transducer elements T1-D32 and selects transducer elements T65-T96, whereby an ultrasonic beam is emitted from point A1 at angle $\theta$, and the corresponding echo is received by the transducer elements corresponding to point B1. Multiplexer 13 then drives elements T2-T33 and selects elements T66-T98, whereby an ultrasonic beam is emitted from point A2 at the same angle θ, and the corresponding echo is received by the transducer elements corresponding to point B2. Further, multiplexer 13 drives elements T3–T34 and selects elements T67–T99, whereby an ultrasonic beam is emitted from point A3 at angle θ, and the corresponding echo is received by the transducer elements corresponding to point B3. Multiplexer 13 functions in this way until an ultrasonic beam is emitted from point An and the corresponding echo is received by the transducer elements corresponding to point Bn. The echo signal which array 11 generates upon receipt of each echo wave is added by adder 23 to any other echo signal generated by array 11, whereby an echo signal having the waveform of FIG. 2C is obtained.

The peak of echo signal shown in FIG. 2C corresponds to that component of the echo which has come from point P. When wave analyzer 24 detects this peak or the address corresponding to the peak, time t is obtained. Therefore, substituting equation (2) in equation (1), we obtain the following equation (4):

$$C = \sqrt{y \cdot C_0/(t \cdot \sin\theta_0)} \quad (4)$$

Hence, sound velocity C can be calculated. More precisely, time t is obtained from known values y, $C_0$ and $\theta_0$. Time t is substituted in equation (4), thereby calculating sound velocity C. Sound velocity C is supplied to display 26 and displayed.

When transducer 11 is driven to output B-Mode image data, display 26 can display a B-Mode image. To reconstruct the B-Mode image, the method disclosed in the above-identified U.S. patent applications can be employed.

In the present invention, parallel ultrasonic beams are emitted at the same angle to a subject, thus scanning the subject, and the echo signals generated from the echoes corresponding to the beams and coming from the subject are added or averaged, thereby containing an echo signal having no ripples resulting from the phenomenon "speckle." Sound velocity C, which has been calculated from this echo signal, is very accurate.

It is preferable to control delay times so that the ultrasonic beams are focussed on each of the targets P1, P2, . . . Pn.

What is claimed is:

1. An ultrasonic measuring apparatus for measuring the sound velocity of an ultrasonic wave propagating through tissue of a subject being examined, said apparatus comprising:

ultrasonic transducer means having an array of transducer elements and having an ultrasonic transmission section comprised of a predetermined number of said elements for emitting a plurality of ultrasonic transmission beams at a predetermined angle with respect to a perpendicular projected from the surface of said array to a plurality of target areas of the subject, and an ultrasonic reception section comprised of a predetermined number of others of said elements of said array separated from said transmission section by a predetermined distance, for receiving echo beams at said predetermined angle reflected from the target areas of said subject and directed to said ultrasonic reception section and for generating echo signals in accordance with said echoes,;

scanning means for driving said ultrasonic transducer means, to scan the subject with the transmission beams and for maintaining said predetermined distance between said ultrasonic transmission and reception sections and said predetermined angle of said transmission beams and echo beams;

signal-processing means for combining a plurality of the echo signals generated by said ultrasonic transducer means;

means for calculating the time which said ultrasonic transmission and echo beams require to propagate through the subject in accordance with the combination of the echo signals which have been obtained by said signal-processing means; and means for calculating the sound velocity of the ultrasonic beams in accordance with the propagation time calculated by said time calculating means.

2. The ultrasonic measuring apparatus according to claim 1, wherein said scanning means comprises pulse-supplying means for supplying drive pulses to said ultrasonic transducer elements which form said ultrasonic transmission section, and signal-extracting means for extracting echo signals from said ultrasonic transducer elements which form said ultrasonic reception section.

3. The ultrasonic measuring apparatus according to claim 2, wherein said pulse-supplying means includes transmission delay means for delaying said drive pulses by such periods that said transmission elements emit ultrasonic beams at said predetermined angle.

4. The ultrasonic measuring apparatus according to claim 2, wherein said signal-extracting means includes reception delay means for delaying said echo signals by time periods determined in accordance with said predetermined angle at which said echo wave is incident upon said elements of said reception section.

5. The ultrasonic measuring apparatus according to claim 1, wherein said scanning means controls said ultrasonic transmission section and ultrasonic reception section of said ultrasonic transducer means to scan the subject in a direction parallel to said surface of said array with said transmission beams emitted at regular intervals.

6. The ultrasonic measuring apparatus according to claim 2, wherein said signal-extracting means includes means for extracting the echo signals at regular time intervals, and memory means for storing the echo signals thus extracted.

7. The ultrasonic measuring apparatus according to claim 1, wherein said propagation time-measuring means measures the propagation time from the peak value of a signal generated by said signal-processing means.

8. The ultrasonic measuring apparatus according to claim 1, wherein said sound velocity-calculating means calculates the sound velocity of the ultrasonic waves in accordance with the following equation:

$$C = \sqrt{y \cdot C_0/(t \cdot \sin\theta_0)}$$

where y is the distance between a beam-emitting point and an echo wave-receiving point, $C_0$ is the sound velocity at which ultrasonic waves propagate in the subject, $\theta_0$ is the angle at which each ultrasonic beam is emitted, and t is the propagation time of the ultrasonic waves.

* * * * *